US008211865B2

(12) United States Patent
Ilan et al.

(10) Patent No.: US 8,211,865 B2
(45) Date of Patent: Jul. 3, 2012

(54) INHIBITION OF ORNITHINE AMINOTRANSFERASE FOR THE TREATMENT OF PROLIFERATIVE DISORDERS

(75) Inventors: Yaron Ilan, Jerusalem (IL); Ehud Zigmond, Jerusalem (IL); Richard B. Silverman, Northbrook (IL); Hejun Lu, Shanghai (CN)

(73) Assignee: Hadasit Medical Research Services & Development, Ltd., Jerusalem (IL)

( * ) Notice: Subject to any disclaimer, the term of this patent is extended or adjusted under 35 U.S.C. 154(b) by 0 days.

(21) Appl. No.: 12/377,889

(22) PCT Filed: Aug. 20, 2007

(86) PCT No.: PCT/IL2007/001034
§ 371 (c)(1),
(2), (4) Date: Sep. 22, 2009

(87) PCT Pub. No.: WO2008/023364
PCT Pub. Date: Feb. 28, 2008

(65) Prior Publication Data
US 2010/0016412 A1  Jan. 21, 2010

(30) Foreign Application Priority Data
Aug. 21, 2006 (IL) .......................................... 177609

(51) Int. Cl.
*A61K 48/00* (2006.01)
(52) U.S. Cl. ..... 514/44; 536/24.5; 536/24.31; 536/24.1; 514/567
(58) Field of Classification Search .................. None
See application file for complete search history.

(56) References Cited

U.S. PATENT DOCUMENTS
2005/0272052 A1  12/2005  Shekar et al.

FOREIGN PATENT DOCUMENTS
EP  1283049 A1  2/2003
WO  02077176 A2  10/2002

OTHER PUBLICATIONS

Shah et al. Structure 1997, Vo. 5(8): 1067-1075.*
Mitchell et al. J. Clin. Invest 1988: 630-633.*
Bence, et al., "The Antiproliferative and Immunotoxic Effects of L-Canavanine and L-Canaline", Anti Cancer Drugs, vol. 13, No. 3, Mar. 2002, pp. 313-320, ISSN 0959-4973.
Colnot, et al., "Liver-Targeted Disruption of Apc in Mice Activates B-Catenin Signaling and Leads to Hepatocellular Carcinomas", Proceedings of the National Academy of Sciences, vol. 101, No. 49, Dec. 7, 2004, pp. 17216-17221, ISSN 0027-8424.
Miyasaka, et al., "Analysis of Differentially Expressed Genes in Human Hepatocellular Carcinoma Using Suppression Subtractive Hybridization", British Journal of Cancer, vol. 85, No. 2, Jul. 2001, pp. 228-234, ISSN 0007-0920.
Naphuket, et al., "Synthesis and Structure-Activity Studies of Some Antitumor Congeners of L-Canaline", Drug Development Research, vol. 47, No. 4, Aug. 1999, pp. 170-177, ISSN 0272-4391.
Rosenthal, G., "L-Canaline: A Potent Antimetabolite and Anti-Cancer Agent From Leguminous Plants", Life Sciences, vol. 60, No. 19, 1997, pp. 1635-1641, ISSN 0024-3205.
Kobayaski, et al., "Studies on the Turnover Rates of Ornithine Aminotransferase in Morris Hepatoma 44 and Host Liver", Journal of Biochemistry, vol. 80, No. 5, 1976, pp. 1085-1089, ISSN 0021-924X.
Zigmond, et al., "Ornithine Aminotransferase (OAT) Gene is Overexpressed in Spontaneously Developed Hepatocellular Carcinoma: Administration of Oat Inhibitor Suppressed Tumor Growth", Hepatology, vol. 44, No. 4, Suppl. 1, Oct. 2006, p. 235A, ISSN 0270-9139.
Lu, H. and Silverman, R.B. (Dec. 14, 2006) *"Fluorinated Conformationally Restricted gamma-Aminobutyric Acid Aminotransferase Inhibitors,"* J. Med. Chem. 49:7404-7412.

* cited by examiner

*Primary Examiner* — Kimberly Chong
(74) *Attorney, Agent, or Firm* — William C. Schrot; Jeffrey I. Auerbach; The Auerbach Law Firm, LLC

(57) ABSTRACT

The invention relates to inhibition of ornithine aminotransferase (OAT) for suppression of tumor cells proliferation. More particularly, the invention relates to methods of treatment of proliferative disorders by the selective inhibition of OAT, and further provides the use of OAT inhibitors, specifically, 5-amino-1,3-hexadienyl-carboxylic acid (Gabaculine), and Gabaculine analogue 8, for compositions and methods for the treatment of proliferative disorders such as hepatocellular carcinoma. The invention further provides methods and kits for the diagnosis of a pathologic proliferative disorder in a mammalian subject, based on determining the level of OAT expressed in a biological sample obtained from a subject.

6 Claims, No Drawings

INHIBITION OF ORNITHINE AMINOTRANSFERASE FOR THE TREATMENT OF PROLIFERATIVE DISORDERS

FIELD OF THE INVENTION

The invention relates to inhibition of ornithine aminotransferase (OAT) for suppression of tumor cells proliferation. More particularly, the invention relates to methods of treatment of proliferative disorders by inhibition of OAT, and further provides the use of OAT inhibitors, for compositions and methods for the treatment of proliferative disorders such as hepatocellular carcinoma.

BACKGROUND OF THE INVENTION

All publications mentioned throughout this application are fully incorporated herein by reference, including all references cited therein.

Cancer of all forms is one of the major causes of morbidity throughout the world. Research in the area of cancer chemotherapy has produced a variety of antitumor agents which have differing degrees of efficacy. A variety of cancer therapeutic agents are known, for example, alkylating agents, antimetabolites, alkaloids and carcinostatic antibiotics. Standard clinically used agents include adriamycin, actinomycin D, methotrexate, 5-fluorouracil, cis platinum, vincristine and vinblastine. However, the presently available antitumor agents are known to have various disadvantages such as toxicity to healthy cells and resistance of certain tumor types.

Hepatocellular carcinoma (HCC) is one of the major malignant diseases in the world today, the greatest incidence being in Japan, China, other parts of the Asia and sub-Saharan Africa. Recent evidence indicates that the incidence of hepatocellular carcinoma in Europe and North America is increasing. The disease is estimated to be responsible for, or involved in, up to approximately 1,250,000 deaths a year, and as such it is numerically one of the world's major malignant diseases.

The prognosis of HCC is poor, with the world-wide frequency rate almost equalling the mortality rate. After diagnosis, the median survival time is less than four months. Long-term survival, defined as survival longer than one year after the diagnosis, is seen only occasionally. Most HCC patients succumb to either the complications of liver failure with or without massive bleeding, or to the general effects of a large tumor burden, with cachexia, malnutrition, infection and sepsis. Though distant metastases occur (up to 90% of patients have metastatic tumors at the time of death), hepatic disease most often limits survival.

Current therapies available to the clinician are on the whole ineffective as a cure for this disease. For patients with advanced HCC who are not candidates for surgical resection, liver transplantation, localized tumor ablation or systemic chemotherapy remains the mainstay of therapy. Unfortunately, HCC is a relatively chemotherapy-resistant proliferative disorder; therefore, outcomes using this mode of treatment are unsatisfactory. Resistance to chemotherapy may be caused by the universal expression of the multidrug resistance gene protein on the surface of the malignant cells, leading to active efflux of chemotherapeutic agents. Chemotherapy is usually not well tolerated and seems to be less efficacious in patients with HCC with underlying hepatic dysfunction. Younger patients with well-compensated cirrhosis due to chronic hepatitis B or C infections have better outcome with chemotherapy than older patients with alcoholic cirrhosis and other comorbid diseases.

The most active single agent drugs tested have been doxorubicin, cisplatin, and fluorouracil. Response rates are about 10%, and treatment shows no clear impact on overall survival. More recently, gemcitabine and capecitabine have been evaluated in clinical trials, but response rates have been low and short term.

A variety of combination chemotherapy regimens have also been studied. Recently, cisplatin-based combination regimens have shown improved response rates around 20%, but to date, no survival advantage as compared to supportive care alone has been shown. No difference seems to exist in response rates between 2 or 3-drug regimens. Moreover, some of these combination regimens cause considerable toxicity.

Chemoimmunotherapy uses a combination of chemotherapy and immunomodulatory agents, such as interferon-alpha, to try to achieve better tumor response rates. Antiangiogenesis agents (i.e., bevacizumab), which work by disrupting the formation of blood vessels that feed tumors, are a new class of drugs that may prove to be of benefit in the treatment of HCC. The highly vascular nature of HCC tumors makes therapy with an antiangiogenesis agent a promising and exciting new option. Further evaluation of these drugs in the setting of clinical trials is needed to determine their efficacy.

Thus, there is a clear need for novel therapeutic approaches for specifically affecting cancerous cells, and especially, HCC. The present invention showed for the first time that ornithine aminotransferase is overexpressed in malignant proliferative tissue. The inventors further showed that inhibition of the enzyme catalytic activity using two different inhibitors, markedly decreased tumor growth, and therefore may be used as a specific target in the treatment of proliferative disorders, and particularly of HCC.

Ornithine aminotransferase (OAT) is a mitochondrial matrix enzyme that catalyzes a reversible reaction of interconversion between ornithine and alpha ketoglutarate to delta-1-pyrroline-5-carboxylate and glutamate. The enzyme is expressed in many tissues, including liver, kidney, small intestine, brain and eye. The enzymes from liver and kidney differ significantly in their regulation, and were believed to be two distinct enzymes. However, DNA sequencing proved that the two enzymes are encoded by a single gene.

As indicated above, glutamate is the product of the reaction catalyzed by OAT. This product can be used as a substrate by glutamine synthetase to synthesize glutamine, which is critical for the growth of proliferative cells, supporting protein and nucleotide synthesis and providing a major source of energy. Therefore an increased activity of OAT could make a tumor cell independent of any glutamine supply and confer a growth advantage to the cell. Thus, without being bound by any theory, it may be hypothesized that reducing the level of tissue glutamine concentrations by inactivation of OAT may lead to inhibition in cell proliferation and tumor growth.

Furthermore, it should be noted that ornithine is a substrate in the urea cycle. The urea cycle is effective in incorporating ammonium ions into urea in order to be eliminated from the body. The present invention is based on inhibition or inactivation of ornithine aminotransferase (OAT). Therefore, alternatively or additionally and without being bound by any theory, it may be postulated that by enhancing the level of tissue ornithine concentrations due to inactivation of OAT over an extended period of time, urea formation in the liver and presumably in some other tissues would be a consequence thereof, thereby lowering blood and cerebrospinal fluid ammonia concentrations. These compounds were implicated in numerous well known human illnesses associated with elevated blood and cerebrospinal fluid ammonia concentrations, among which, for example, are liver cirrhosis, fulminant hepatic failure and urinary tract/bladder infections. These, and particularly cirrhosis, may therefore lead to HCC.

Thus, the present invention comprises the new use of OAT inhibitors, for the treatment of proliferative disorders.

It is thus one object of the invention to provide a method for the treatment of proliferative disorders, and particularly HCC, which is based on inhibiting the expression or the activity of ornithine aminotransferase (OAT).

Another object of the invention is the use of ornithine aminotransferase inhibitors, and particularly of Gabaculine and Gabaculine analogue 8, for the preparation of pharmaceutical composition for the treatment of malignant proliferative disorders.

Another object of the invention is to provide for a diagnostic method for detection of proliferative disorders, particularly of HCC, by detecting increase in the expression of ornithine aminotransferase.

These and other objects of the invention will become apparent as the description proceeds.

SUMMARY OF THE INVENTION

In a first aspect the present invention relates to a method for the treatment of a pathologic proliferative disorder in a subject in need thereof. The method of the invention is based on selectively inhibiting ornithine aminotransferase (OAT) in the treated subject.

According to one embodiment, the inhibition of ornithine aminotransferase (OAT) may be achieved by inhibiting the expression or by inhibiting the enzymatic activity of this enzyme.

In a specifically preferred embodiment, inhibiting the enzymatic activity of ornithine aminotransferase (OAT) may be performed by administering to the treated subject an inhibitory effective amount of OAT inhibitor selected from the group consisting of 5-amino-1,3-hexadienyl-carboxylic acid (Gabaculine), Gabaculine analogue 8 (LHJ-II-79), 5-fluoromethylornithine (6-fluoro-2,5-diaminohexanoic acid, 5-FMOrn) and (S)-2-amino-4-amino-oxybutyric acid (Canaline). More preferably, the inhibitor may be 5-amino-1,3-hexadienyl-carboxylic acid (Gabaculine). According to another preferred embodiment, the inhibitor may be Gabaculine analogue 8 (LHJ-II-79).

In a second aspect, the invention relates to a pharmaceutical composition for the treatment of a pathologic proliferative disorder. The composition of the invention comprises as an active ingredient an ornithine aminotransferase (OAT) inhibitor, that may be capable of inhibiting the expression or the enzymatic activity of said OAT.

In a further aspect, the invention provides for the use of an ornithine aminotransferase (OAT) inhibitor for the preparation of a pharmaceutical composition for the treatment of a pathologic proliferative disorder in a subject in need thereof.

In a fourth aspect, the invention relates to a diagnostic method for diagnosis of a pathologic proliferative disorder. The diagnostic method of the invention comprises the steps of: (a) determining the level of OAT expressed in a biological sample obtained from said subject; (b) determining the level of one or more control genes expressed in said biological sample obtained from said subject; and (c) comparing the level of expression of OAT in said sample according to step a) and the level of expression of each of said one or more control genes in said sample according to step b) with the level of OAT and the level of one or more control reference genes in a control sample; wherein detecting differential expression of OAT in the comparison of step c) is indicative of that said subject is suffering of said proliferative disorder.

The invention further provides kits for the diagnosis of pathologic proliferative disorders.

These and more aspects of the invention will become apparent in hand of the following examples.

DETAILED DESCRIPTION OF THE INVENTION

In a first aspect the present invention relates to a method for the treatment of a pathologic proliferative disorder in a subject in need thereof. The method of the invention is based on the step of selectively inhibiting ornithine aminotransferase (OAT) in the treated subject.

According to one embodiment, the inhibition of ornithine aminotransferase (OAT) may be achieved by inhibiting the expression or by inhibiting the enzymatic activity of this enzyme.

In a specifically preferred embodiment, inhibiting the enzymatic activity of ornithine aminotransferase (OAT) may be performed by administering to the treated subject an inhibitory effective amount of OAT inhibitor selected from the group consisting of 5-amino-1,3-hexadienyl-carboxylic acid (Gabaculine), Gabaculine analogue 8 (LHJ-II-79), 5-fluoromethylornithine (6-fluoro-2,5-diaminohexanoic acid, 5-FMOrn) and (S)-2-amino-4-amino-oxybutyric acid (Canaline. More preferably, the inhibitor may be 5-amino-1,3-hexadienyl-carboxylic acid (Gabaculine). It should be noted that Gabaculine has the following molecular formula: $C_7H_9NO_2$, and its molecular weight is 139.152 g/mol.

According to another preferred embodiment, the inhibitor may be Gabaculine analogue 8 (LHJ-II-79). It should be appreciated that this analogue has the following chemical name: 1-carboxy-3-amino-4-bis(trifluoromethyl)vinylidene cyclopentane hydrochloride and has the following molecular formula: $C_9O_2N_1Cl_1F_6H_8$.

It should be noted that any derivatives and stereoisomers of these inhibitors are also contemplated within the scoop of the invention. The term "stereoisomer" is a general term for all isomers of individual molecules that differ only in the orientation of their atoms in space. It includes mirror image isomers (enantiomers), geometric (cis/trans) isomers, and isomers of compound with more than one chiral center that are not mirror images of one another (diastereoisomers).

According to an alternative embodiment, inhibition of OAT may be achieved by inhibition of the expression of this enzyme. The expression of ornithine aminotransferase (OAT) may be inhibited by administering to the treated subject an inhibitory effective amount of a nucleic acid molecule comprising at least one target specific sequence, which sequence is complementary to a target ribonucleotide sequence comprised within OAT mRNA.

It should be appreciated that according to a specific embodiment the OAT is the human OAT as referred to by the mRNA sequence of GenBank Accession No. NM_000274, as encoded by genomic region 166400-187979 of human chromosome 10, referred to in GenBank Accession No. NT 035040, incorporated herein by reference.

More specifically, a nucleic acid molecule may be selected from the group consisting of an antisense DNA or RNA molecule, a ribonucleic acid molecule having endonuclease activity (ribozyme) and a small interfering RNA (siRNA) specific for said OAT.

The term "nucleic acid" refers to a polymer of nucleotides, or a polynucleotide, as described above. The term is used to designate a single molecule, or a collection of molecules.

Nucleic acids may be single stranded or double stranded, and may include coding regions and regions of various control elements, as described below.

According to one embodiment, inhibition of OAT expression may be performed using an anti-sense technology. By "antisense nucleic acid" it is meant a non-enzymatic nucleic acid molecule that binds to target RNA by means of RNA-RNA or RNA-DNA or RNA-PNA (protein nucleic acid) interactions and alters the activity of the target RNA. Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "complementarity" is meant that a nucleic acid can form hydrogen bond(s) with another nucleic acid sequence by either traditional Watson-Crick or other non-traditional types. In reference to the nucleic molecules used by the present invention, the binding free energy for a nucleic acid molecule with its target or complementary sequence is sufficient to allow the relevant function of the nucleic acid to proceed, e.g., ribozyme cleavage, recruitment of RICA by siRNA.

Inhibition of OAT expression may be performed according to another specific embodiment, using ribozyme specific for OAT. Ribozymes are RNA molecules having an enzymatic activity which is able to repeatedly cleave other separate RNA molecules in a nucleotide base sequence specific manner. It is said that such enzymatic RNA molecules can be targeted to virtually any RNA transcript and efficient cleavage has been achieved in vitro.

Six basic varieties of naturally-occurring enzymatic RNAs are known presently. Each can catalyze the hydrolysis of RNA phosphodiester bonds in-trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

In yet another specific embodiment, siRNA may be used by the method of the invention for inhibiting the expression of OAT. The term "siRNAs" refers to short interfering RNAs. The term "RNA interference" or "RNAi" refers to the silencing or decreasing of gene expression by siRNAs. It is the process of sequence-specific, post-transcriptional sequence-specific gene silencing in animals and plants, initiated by siRNA that is homologous in its duplex region to the sequence of the silenced gene. The gene may be endogenous or exogenous to the organism, integrated into a chromosome or present in a transfection vector which is not integrated into the genome. The expression of the gene is either completely or partially inhibited. RNAi may also inhibit the function of a target RNA, and said function may be completely or partially inhibited.

RNAi is a multistep process. In a first step there is cleavage of large dsRNAs, through the action of the Dicer enzyme (an RNase III endonuclease), into 21-23 ribonucleotides-long double stranded effector molecules called small interfering RNAs (siRNAs). These siRNAs duplexes then associate with an endonuclease-containing complex, known as RNA-induced silencing complex (RISC). The RISC specifically recognizes and cleaves the endogenous mRNAs containing a sequence complementary to one of the siRNA strands. One of the strands of the double-stranded siRNA molecule comprises a nucleotide sequence that is complementary to a nucleotide sequence of the endogenous mammalian target gene, specifically OAT or a portion thereof, and the second strand of the double-stranded siRNA molecule comprises a nucleotide sequence substantially similar to the nucleotide sequence of the endogenous mammalian target gene (OAT) or a portion thereof.

In some embodiments, siRNAs comprise a duplex, or double-stranded region, of about 18-25 nucleotides long. Often siRNAs contain from about two to four unpaired nucleotides at the 3' end of each strand. At least a portion of one strand of the duplex or double-stranded region of a siRNA is substantially homologous to or substantially complementary to a target sequence within OAT RNA molecule. The strand complementary to a target RNA molecule is the "antisense strand", the strand homologous to the target RNA molecule is the "sense strand" (which is also complementary to the siRNA antisense strand). siRNAs may also contain additional sequences. Non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing.

It should be appreciated that inhibition of OAT expression or activity may be achieved by a combination therapy combining any of the expression or activity inhibitors described above.

The term "combination therapy" can mean concurrent or consecutive administration of two or more agents. For example, concurrent administration can mean one dosage form in which the two or more agents are contained whereas consecutive administration can mean separate dosage forms administered to the patient at different times and maybe even by different routes of administration.

In yet another embodiment, the method of the invention is intended for the treatment of pathologic proliferative disorder.

As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

According to a preferred embodiment, the method of the invention is specifically applicable for the treatment of malignant proliferative disorders. As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors.

In general, the methods and compositions of the present invention may be used in the treatment of non-solid and solid tumors.

Malignancy, as contemplated in the present invention may be selected from the group consisting of melanomas, carcinomas, leukemias, lymphomas and sarcomas. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including bladder, rectum, stomach, cervix, ovarian, renal, lung, liver, breast, colon, prostate GI tract, pancreas and Karposi). More particularly, according to a preferred embodiment, the OAT inhibitors used by the method of the invention or any composition comprising the same according to the invention, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma, retinoblastoma, carcinoma of the lacrimal gland, sarcoma of the orbit, brain, spinal cord, vascular system, hemangiosarcoma and Kaposi's sarcoma.

According to a specifically preferred embodiment, the method of the invention is particularly applicable for the treatment of hepaotcellular carcinoma (HCC).

It should be noted that all disorders indicated herein as disorders that may be treated by the methods of the invention, may also be treated by the compositions of the invention described herein after.

According to another embodiment, the different inhibitors of OAT, may be administered according to the method of the invention in any suitable way. For example, administration comprises oral, intravenous, intraarterial, intramuscular, subcutaneous, intraperitoneal, parenteral, transdermal, intravaginal, intranasal, mucosal, sublingual, topical, rectal or subcutaneous administration, or any combination thereof.

According to another embodiment, the treated subject may be a mammalian subject. Although the methods of the invention are particularly intended for the treatment of proliferative disorders in humans, other mammals are included. By way of non-limiting examples, mammalian subjects include monkeys, equines, cattle, canines, felines, mice, rats and pigs.

The terms "treat, treating, treatment" as used herein and in the claims mean ameliorating one or more clinical indicia of disease activity in a patient having a pathologic disorder.

"Treatment" refers to therapeutic treatment. Those in need of treatment are mammalian subjects suffering from any pathologic disorder. By "patient" or "subject in need" is meant any mammal for which administration of the OAT inhibitors, or any pharmaceutical composition of the invention is desired, in order to prevent, overcome or slow down such infliction.

To provide a "preventive treatment" or "prophylactic treatment" is acting in a protective manner, to defend against or prevent something, especially a condition or disease.

The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

As shown by Example 3, in vivo injection of 500 µg/kg of body weight of the Gabaculine inhibitor significantly suppressed tumor growth. Based on these results, a daily amount of such preferred inhibitor may contain between about 0.01 to 5000, preferably, 0.5 to 50 mg per kg of body weight of the Gabaculine inhibitor.

Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

In a second aspect, the invention relates to a pharmaceutical composition for the treatment of a pathologic proliferative disorder. The composition of the invention comprises as an active ingredient an ornithine aminotransferase (OAT) inhibitor, that may be capable of inhibiting the expression or the enzymatic activity of said OAT.

According to one specific embodiment, the composition of the invention may comprise as an active ingredient an ornithine aminotransferase (OAT) inhibitor selected from the group consisting of 5-amino-1,3-hexadienyl-carboxylic acid (Gabaculine), Gabaculine analogue 8 (LHJ-II-79), 5-fluoromethylornithine (6-fluoro-2,5-diaminohexanoic acid, 5-FMOrn) and (S)-2-amino-4-amino-oxybutyric acid (Canaline).

According to a specifically preferred embodiment, the composition of the invention comprises as an active ingredient the OAT inhibitor, 5-amino-1,3-hexadienyl-carboxylic acid (Gabaculine).

According to another specifically preferred embodiment, the composition of the invention comprises as an active ingredient the OAT inhibitor, Gabaculine analogue 8 (LHJ-II-79).

In an alternative embodiment, the composition of the invention comprises as an active ingredient an OAT inhibitor that may be a nucleic acid molecule comprising at least one target specific sequence, which sequence is complementary to a target ribonucleotide sequence comprised within OAT mRNA. More specifically, such nucleic acid molecule may be selected from the group consisting of an antisense DNA or RNA molecule, a ribonucleic acid molecule having endonuclease activity (ribozyme) and a small interfering RNA (siRNA) specific for said OAT.

According to another preferred embodiment, the composition of the invention is intended for the treatment of a pathologic proliferative disorder, preferably, a malignant proliferative disorder of any one of solid and non-solid tumor selected from the group consisting of carcinoma, sarcoma, melanoma, lymphoma and leukemia. More specifically, the composition of the invention is particularly applicable for the treatment of carcinoma such as liver, breast, bladder, rectum, stomach, cervix, ovarian, colon, renal or prostate carcinoma.

According to a specifically preferred embodiment, the composition of the invention is intended for the treatment of hepatocellular carcinoma (HCC).

The pharmaceutical compositions of the invention generally comprise a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

The invention further relates to an ornithine aminotransferase (OAT) inhibitor for use in the treatment of pathologic proliferative disorders in a subject in need thereof.

In a further aspect, the invention provides for the use of an ornithine aminotransferase (OAT) inhibitor for the preparation of a pharmaceutical composition for the treatment of a pathologic proliferative disorder in a subject in need thereof.

According to one embodiment, the ornithine aminotransferase (OAT) inhibitor used by the invention may be capable of inhibiting OAT enzymatic activity, such inhibitor may be selected from the group consisting of 5-amino-1,3-hexadienyl-carboxylic acid (Gabaculine), Gabaculine analogue 8 (LHJ-II-79), 5-fluoromethylornithine (6-fluoro-2,5-diaminohexanoic acid, 5-FMOrn) and (S)-2-amino-4-amino-oxybutyric acid (Canaline). According to a specifically preferred embodiment, the inhibitor may be 5-amino-1,3-hexadienyl-carboxylic acid (Gabaculine). According to another specifically preferred embodiment, the inhibitor may be Gabaculine analogue 8 (LHJ-II-79).

In yet another alternative embodiment, the invention provides the use of a nucleic acid molecule comprising at least one target specific sequence, which sequence is complementary to a target ribonucleotide sequence comprised within OAT mRNA, as an OAT inhibitor.

More specifically, the nucleic acid molecule may be a ribonucleic acid molecule selected from the group consisting of an antisense DNA or RNA molecule, a ribonucleic acid molecule having endonuclease activity (ribozyme) and a small interfering RNA (siRNA) specific for said OAT.

According to another embodiment, the invention relates to the use of different OAT inhibitors for the preparation of composition for the treatment of a malignant pathologic proliferative disorder such as solid and non-solid tumor selected from the group consisting of carcinoma, sarcoma, melanoma lymphoma and leukemia.

More particularly, such carcinoma may be a liver, breast, bladder, rectum, stomach, cervix, ovarian, colon, renal or prostate carcinoma.

According to a specifically preferred embodiment, the invention relates to the use of different OAT inhibitors for the preparation of composition for the treatment of hepatocellular carcinoma (HCC).

In a fourth aspect, the invention relates to a diagnostic method for the diagnosis of a pathologic proliferative disorder. The diagnostic method of the invention comprises the steps of (a) determining the level of OAT expressed in a biological sample obtained from said subject; (b) determining the level of one or more control genes expressed in said biological sample obtained from said subject; and (c) comparing the level of expression of OAT in said sample according to step a) and the level of expression of each of said one or more control genes in said sample according to step b) with the level of OAT and the level of one or more control reference genes in a control sample. It should be noted that detecting differential expression of OAT in the comparison of step c) is indicative of that said subject is suffering of said proliferative disorder.

It should be noted that the diagnostic method of the invention is based on the finding that OAT is over expressed in samples of HCC. This differential expression is the basis for the development of the diagnostic method of the invention. "Differentially expressed" can also include a measurement of the RNA or protein encoded by the OAT gene of the invention in a sample or population of samples as compared with the amount or level of RNA or protein expression in a second sample or population of samples. Differential expression can be determined as described herein and as would be understood by a person skilled in the art. The term "differentially expressed" or "changes in the level of expression" refers to an increase or decrease in the measurable expression level of the OAT gene as measured by the amount of RNA and/or the amount of protein in a sample as compared with the measurable expression level of the OAT gene in a second sample. The term "differentially expressed" or "changes in the level of expression" can also refer to an increase or decrease in the measurable expression level of the OAT gene in a population of samples as compared with the measurable expression level of the OAT gene in a second population of samples. As used herein, "differentially expressed" can be measured using the ratio of the level of expression of the OAT gene as compared with the mean expression level of the OAT gene of a control wherein the ratio is not equal to 1.0. Differentially expressed can also be measured using p-value. When using p-value, the OAT gene is identified as being differentially expressed as between a first and second population when the p-value is less than 0.1. More preferably the p-value is less than 0.05. Even more preferably the p-value is less than 0.01. More preferably still the p-value is less than 0.005. Most preferably the p-value is less than 0.001. When determining differentially expression on the basis of the ratio, an RNA or protein is differentially expressed if the ratio of the level of expression in a first sample as compared with a second sample is greater than or less than 1.0. For example, a ratio of greater than 1.2, 1.5, 1.7, 2, 3, 4, 10, 20 or a ratio less than 1, for example 0.8, 0.6, 0.4, 0.2, 0.1. 0.05. In another embodiment of the invention a nucleic acid transcript or is differentially expressed if the ratio of the mean of the level of expression of a first population as compared with the mean level of expression of the second population is greater than or less than 1.0 For example, a ratio of greater than 1.2, 1.5, 1.7, 2, 3, 4, 10, 20 or a ratio less than 1, for example 0.8, 0.6, 0.4, 0.2, 0.1. 0.05. In another embodiment of the invention a nucleic acid transcript or is differentially expressed if the ratio of its level of expression in a first sample as compared with the mean of the second population is greater than or less than 1.0 and includes for example, a ratio of greater than 1.2, 1.5, 1.7, 2, 3, 4, 10, 20, or a ratio less than 1, for example 0.8, 0.6, 0.4, 0.2, 0.1. 0.05.

More specifically, "Differentially increased expression" or "up regulation" refers to genes, such as the OAT gene, which demonstrate at least 10% or more, for example, 20%, 30%, 40%, or 50%, 60%, 70%, 80%, 90% or more or 1.1 fold, 1.2 fold, 1.4 fold, 1.6 fold, 1.8 fold, or more increase in gene expression (as measured by RNA expression or protein expression), relative to a control.

The term "overexpression" refers to the production of a gene product in an organism or a certain tissue that exceeds levels of production in normal organisms or tissues. Example 1, clearly demonstrate overexpression of OAT in HCC cells compared to normal cells.

"Differentially decreased expression" or "down regulation" refers to genes which demonstrate at least 10% or more, for example, 20%, 30%, 40%, or 50%, 60%, 70%, 80%, 90% or a less than 1.0 fold, 0.8 fold, 0.6 fold, 0.4 fold, 0.2 fold, 0.1 fold or less decrease in gene expression (as measured by RNA expression or protein expression), relative to a control.

A gene expression pattern of the OAT gene can result from the measurement of expression of the RNA or protein products of the OAT gene of the invention and can be done using any known technique. For example techniques to measure expression of the RNA products of the OAT gene of the invention includes, PCR based methods (including RT-PCR) and non PCR based method as well as micro-array analysis. To measure protein products of the OAT gene of the invention, techniques include western blotting and ELISA analysis.

More particularly, according to one embodiment, determination of the expression of the OAT gene according to step (a) and determination of the expression of one or more control reference genes according to step (b) of the method of the invention, may be performed by a method comprising the step of contacting said sample or any nucleic acid or amino acid product obtained therefrom with at least one detecting molecule or a collection of at least two detecting molecules specific for determination of the expression of the OAT gene and of one or more control reference genes.

It should be appreciated that the detection step may be performed using the tested sample as obtained from the tested subject, or alternatively, may be performed using any constituent or material derived or prepared therefrom. As a non-limiting example, it should be noted that the method of the invention further encompasses the use of nucleic acid molecules and or proteins prepared from the tested sample.

According to one preferred embodiment the detecting molecule used for the diagnostic method of the invention may be an isolated nucleic acid molecule or an isolated amino acid molecule, or any combination thereof.

According to one alternative and preferred embodiment, the method of the invention uses as a detecting molecule an isolated nucleic acid molecule. More specifically, such nucleic acid molecule may be an isolated oligonucleotide which specifically hybridizes to a nucleic acid sequence of the RNA products of OAT.

Accordingly, the expression of the OAT gene and of the control reference gene may be determined according to a preferred embodiment, using a nucleic acid amplification assay such as PCR, Real Time PCR, micro arrays, in situ Hybridization and Comparative Genomic Hybridization.

According to an alternative embodiment, the method of the invention uses an isolated amino acid molecule as the detecting molecule. Such detecting molecule may be therefore an isolated polypeptide which binds selectively to the protein product of OAT.

Accordingly, the detecting molecule for the control reference genes may be an isolated polypeptide which binds selectively to a protein product of at least one control reference gene. Such control genes may be for example, HSPCB, RPS9, RPL32 or β-actin.

According to a specifically preferred embodiment, the detecting molecule may be an isolated antibody. In such case, according to another embodiment of the invention, the expression may be determined using an immunoassay selected from the group consisting of an ELISA, a RIA, a slot blot, a dot blot, immunohistochemical assay, FACS, a radio-imaging assay or a Western blot.

It should be appreciated that in case the detecting molecule may be an anti-OAT antibody, the antibody used for of the invention may be a monoclonal or polyclonal antibody.

It should be noted that the term "antibody" is meant to include intact molecules as well as fragments thereof, such as, for example, Fab and F(ab')2, which are capable of binding antigen.

It will be appreciated that Fab and F(ab')$_2$ and other fragments of the antibodies are within the scope of the present invention and may be used for the kits and the diagnostic methods disclosed herein for intact antibody molecules. Such fragments are typically produced by proteolytic cleavage, using enzymes such as papain (to produce Fab fragments) or pepsin (to produce F(ab')2 fragments).

In a further embodiment, the diagnostic method of the invention is intended for the diagnosis and monitoring of a pathological disorder in a mammalian subject.

According to one embodiment of the invention the biological sample is malignant, e.g., it is a solid tumor or hematopoietic tumor sample. The solid tumor can, for example, be of the types: carcinoma, glyoma, adenocarcinoma, squameous cell carcinoma, teratocarcinoma, mesothelioma or melanoma. The hematopoietic tumor can, for example, be lymphoma or leukemia. In some embodiments of the present invention the solid tumor is a primary tumor, or a metastasis thereof, and it originates from an organ such as, for example, liver, prostate, bladder, breast, ovary, cervix, colon, skin, intestine, stomach, uterus (including embryo) and pancreas. These conditions include myeloma, breast carcinoma and metastatic breast carcinoma.

The present invention relates, in some embodiments, to diagnostic assays, which in some embodiments, utilizes a biological sample taken from a subject (patient), which for example may comprise any biological sample, such as body fluid or secretion including but not limited to seminal plasma, blood, serum, urine, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system, lavage of any other part of the body or system in the body, samples of any organ including but not limited to lung, colon, ovarian and/or breast tissue, faeces or a tissue sample, any cells derived therefrom, or any combination thereof. In some embodiments, the term encompasses samples of in vitro or ex vivo cell culture or cell culture constituents. The sample can optionally be diluted with a suitable eluant before contacting the sample with the detecting molecule/s of the invention and/or performing any other diagnostic assay.

As used herein, "patient", "subject" or "individual" refers to a mammal, preferably human, who is diagnosed by the method of the invention.

As used herein, the term "control" or "control sample" includes positive or negative controls. In the context of this invention the term "positive control" refers to one or more samples isolated from an individual or group of individuals who are classified as suffering of a pathologic proliferative disorder. The term "negative control" refers to one or more samples isolated from an individual or group of individuals who are healthy subjects.

The invention further provides a diagnostic kit for non-invasive detection and monitoring of a pathologic disorder in a mammalian subject. The kit of the invention may comprise: (a) means for obtaining a sample of said subject; (b) at least one detecting molecule or a collection of at least two detecting molecules specific for determination of the expression of OAT.

It should be noted that the kit of the invention may optionally comprise, (c) at least one detecting molecule or a collection of at least two detecting molecules specific for determination of the expression of at least one control reference gene or a collection of at least two control reference genes. Such control reference genes may be HSPCB, RPS9, RPL32 or β-actin. The kit of the invention further comprises (d) at least one control sample selected from at least one of a negative control sample and a positive control sample; (e) instructions for carrying out the detection and quantification of expression of said OAT and of at least one control reference gene in said sample; and (f) instructions for evaluating the differential expression of said OAT in said sample and optionally of a control reference gene in said sample as compared to the expression of said OAT and optionally control reference gene in said control sample.

According to one embodiment, the detecting molecule comprised within the kit of the invention may be an isolated nucleic acid molecule or an isolated amino acid molecule, or any combination thereof.

According to one specific and preferred embodiment, the detecting molecule comprised within the kit of the invention may be an isolated nucleic acid molecule. Such molecule may be preferably, an isolated oligonucleotide which specifically hybridizes to a nucleic acid sequence of the RNA products of OAT.

According to a preferred embodiment, such oligonucleotide may be a pair of primer or nucleotide probe or any combination, mixture or collection thereof.

According to another preferred optional embodiment, the kit of the invention may further comprise at least one reagent for performing a nucleic acid amplification based assay. Such nucleic acid amplification assay may be any one of PCR, Real Time PCR, micro arrays, in situ Hybridization and Comparative Genomic Hybridization.

According to a specifically preferred embodiment such detecting molecule may be an isolated antibody.

It should be noted that the kit of the invention may optionally further comprises at least one reagent for performing an immuno assay, such as ELISA, a RIA, a slot blot, a dot blot, immunohistochemical assay, FACS, a radio-imaging assay, Western blot or any combination thereof.

According to a preferred embodiment, the kits provided by the invention may further comprise suitable means and reagents for preparing or isolating at least one of nucleic acids and amino acids from the examined sample.

In another embodiment, the present invention relates in part to kits comprising sufficient materials for performing one or more methods described herein. In preferred embodiments, a kit includes one or more materials selected from the following group in an amount sufficient to perform at least one assay.

Thus, according to another preferred optional embodiment, the kit of the invention may further comprise at least one reagent for performing a nucleic acid amplification based assay. Such nucleic acid amplification assay may be any one of PCR, Real Time PCR, micro arrays, in situ Hybridization and Comparative Genomic Hybridization.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key' gene of interest is expressed, but rather to provide other useful information, such as background or basal level of expression. Such control samples may be for example, HSPCB, RPS9, RPL32 and β-actin. Optionally, other control nucleic acids may be spotted on the array and used as target expression control nucleic acids.

According to an alternative embodiment, the detecting molecule comprised within the kit of the invention may be an isolated amino acid molecule, for example, an isolated polypeptide which binds selectively to the protein product of OAT It should be noted that the kit of the invention may therefore further comprises at least one reagent for performing an immuno assay, such as ELISA, a RIA, a slot blot, a dot blot, immunohistochemical assay, FACS, a radio-imaging assay, Western blot or any combination thereof.

According to a preferred embodiment, the kits provided by the invention may further comprise suitable means and reagents for preparing or isolating at least one of nucleic acids and amino acids from said sample.

For RT-PCR kits, the kits generally comprise pre-selected primers specific for particular RNA products (e.g., an exon(s), an intron(s), an exon junction(s), and an exon-intron junction(s)) of the OAT gene of the invention. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for RNA products of the OAT gene of the invention. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay.

For antibody based kits, the kit can comprise, for example: (1) a first antibody (which may or may not be attached to a support) which binds to protein of interest (e.g., a protein product of the OAT gene of the invention); and, optionally, (2) a second, different antibody which binds to either the protein, or the first antibody and is conjugated to a detectable label (e.g., a fluorescent label, radioactive isotope or enzyme).

The antibody-based kits may also comprise beads for conducting an immunoprecipitation.

Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

It should be thus appreciated that any of the kits of the invention may optionally further comprises solid support, such as plates, beads, tube or containers. These may be specifically adopted for performing different detection steps or any nucleic acid amplification based assay or immuno assay, as described for example by the method of the invention. It should be further noted that any substance or ingredient comprised within any of the kits of the invention may be attached, embedded, connected or linked to any solid support.

It should be noted that any of the detecting molecules used by the compositions, methods and kits of the invention may be labeled by a detectable label. The term "detectable label" as used herein refers to a composition or moiety that is detectable by spectroscopic, photochemical, biochemical, immunochemical, electromagnetic, radiochemical, or chemical means such as fluorescence, chemifluoresence, or chemiluminescence, or any other appropriate means. Preferred detectable labels are fluorescent dye molecules, or fluorochromes, such fluorescein, phycoerythrin, CY3, CY5, allophycocyanine, Texas Red, peridenin chlorophyll, cyanine, FAM, JOE, TAMRA, tandem conjugates such as phycoerythrin-CY5, and the like. These examples are not meant to be limiting.

It is to be understood that any polynucleotide or polypeptide or any combination thereof described by the invention may be useful as a marker for a disease, disorder or condition, and such use is to be considered a part of this invention.

It should be appreciated that all method and kits described herein, preferably comprises any of the compositions of the invention.

It should be recognized that the nucleic acid sequences and/or amino acid sequences used by the kits of the present invention relate, in some embodiments, to their isolated form, as isolated polynucleotides (including for all transcripts), oligonucleotides (including for all segments, amplicons and primers), peptides (including for all tails, bridges, insertions or heads, optionally including other antibody epitopes as described herein) and/or polypeptides (including for all proteins). It should be noted that the terms "oligonucleotide" and "polynucleotide", or "peptide" and "polypeptide", may optionally be used interchangeably.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Animal Models
  *Psammomys obesus* (sand rat)—Harlan, Jerusalem, Israel.
  Athymic Balb/c mice—Harlan, Jerusalem, Israel.
Cell Lines
  CT-26: is a mouse cell line, provided by ATCC Cat. No. CRL-2638.
  HUH7: H. is a human cell line described by Nakabyashi et al, Cancer Research, 42: 3858-3863 (1982).
  skhep1: is a human cell line, provided by ATCC Cat. No. UTB 52.
  HepA1-6: a mouse cell line, described by Dalington G. J. et al., J. Nat Cancer Institute, 64:809-819 (1980).
  Hep3b-human hepatocellular carcinoma cell line. ATCC™ Cat. No. HB-8064™.
  PLC/REF/5: is a human cell line, provided by ATCC™ Cat. No. CRL-2711.
  FLC4: is a human cell line, described by Aoki Y. et al, Virogloy 250:140-150 (1998).
  HepG2: is a human cell line, provided by ATCC Cat. No. HB-8065.
  LS-180: is a human cell line, provided by ATCC Cat. No. CL-187.
HCC Cell Line Culture Medium
  500 ml Mem-Eagle (Earle's), 10% Fetal Calf serum, Penicillin/streptomycin, Sodium bicarbonates 1.5 g/L, Non-essential amino acids 0.1 Mm and Sodium pyruvate 1 mM.
OAT Inhibitors
  5-amino-1,3-hexadienyl-carboxylic acid (Gabaculine), purchased from SIGMA-ALDRICH Inc, Saint Louis, Mo., USA, Cat. No. A3539.
  Gabaculine analogue 8 (LHJ-II-79), which has the following chemical name: 1-carboxy-3-amino-4-bis(trifluoromethyl)vinylidene cyclopentane hydrochloride ($C_9O_2N_1Cl_1F_6H_8$).
DNA Microarray
  For performing the DNA microarray analysis, total RNA was extracted from liver tumors and from normal liver tissue of *Psammomys obesus*. RNA extraction was repeated from three different tumors and used in three different arrays. Contamination by DNA was eliminated by treatment of the RNA with DNAse. Total RNA was used for the synthesis of cDNA. cDNAs of the tumor and the normal tissue were labeled with different dyes and loaded on micro array containing the whole mice genome, and exposure signals were scanned and quantified. Taking into consideration the variability attendant upon any biological system, in analyzing the cDNA arrays, the inventors focused only on genes that were differentially upregulated or downregulated in all the three liver tumors.

Treatment of HCC Cell Lines with Gabaculine $10^5$ cells of each of the cell lines were grown in 96 wells plates in triplicates. Gabaculine (2000 micro mol/liter) was added for 48 hours. Thymidine incorporation assay and measurement of Alpha Feto-Protein level were performed.

Treatment of HCC Cell Lines with Gabaculine Analogue 8 (LHJ-II-79)

$1 \times 10^5$ cells/well of each of Hep3b and HepG2 hepatocellular carcinoma cell lines were plated in triplicate and incubated at 37° C. Gabaculine analogue 8 was added to wells at varying concentrations (0.1 μg/ml, 1 μg/ml, 10 μg/ml and 50 μg/ml). Cells returned to incubator for further incubation of 48 hours. In the fourth day of the experiment, one ml of supernatant from each well was transferred to eppendorf tubes and analyzed for αFP concentration. αFP levels were checked using the Abbott Diagnostic AxSYM system.

Example 1

Ornithine Aminotransferase (OAT) Overexpression in HCC Tissue

The *Psammomys obesus* (sand rat) develops spontaneous hepatocellular carcinoma (HCC), and was therefore used by the present inventors as a model of proliferative disorder, and more particularly, as a model for hepatocellular carcinoma. The aim of the present study was to identify genes associated with liver tumorogenesis using the sand rat model and to assess whether specific inhibition of the protein products of such genes may suppress HCC growth.

Identification of genes which are overexpressed in hepatocellular carcinoma tissue was performed using comparative DNA microarray-based gene expression profiling assay of HCC and normal liver tissue, in a spontaneous HCC-developing sand rat model. Statistical analysis of microarray data revealed seven genes whose expression levels were increased by two logs or more in multiple tumors tissues, when compared to normal liver. One of the most prominent of these genes was ornithine aminotransferase (OAT).

As indicated in the background of the invention, OAT is a mitochondrial enzyme that catalyses the transamination of ornithine to glutamate, and was found to be a beta-catenin target gene.

Example 2

Inhibition of OAT Leads to Inhibition of HCC Cell Lines Proliferation

The significant increase in OAT expression in HCC liver tissue, and the fact that overexpression of OAT enables extracellular glutamine independent cell growth, which may be advantageous in tumor proliferation, have led the inventors to investigate the potential effect of OAT inhibition on HCC proliferation.

5-Amino-1,3-hexadienyl-carboxylic acid (Gabaculine) is known as a potent OAT inhibitor. Gabaculine was next tested in vitro on ten different HCC cell lines. 48 hrs following exposure to Gabaculine, cell proliferation (Table 1) and alpha feto protein (AFP) secretion (Table 2) were evaluated.

As clearly demonstrated by Table 1, in vitro application of Gabaculine on different HOC cell lines significantly suppressed the proliferation. This effect was clearly shown in three HCC cell lines (Hep3B, PLC and HepA1-6 cell lines, by 46 to 51% p<0.05).

As shown by Table 2, alpha feto protein (AFP) secretion analysis, indicated that Gabaculine significantly decreased AFP secretion by 20% in Hep3B cells (p<0.0005).

TABLE 1

Gabaculine decreases HCC cell proliferation
HCC Lines Proliferation CPM-B with Gabaculine (20000 umol/L)

|  | CT-26 | HUH7 | skhep1 | HepA1-6 | PLC/REF/5 |
| --- | --- | --- | --- | --- | --- |
| Line | 452 | 303 | 289 | 598 | 543 |
| Line | 398 | 436 | 207 | 739 | 460 |
| Line |  | 391 | 238 | 434 |  |
| Line |  |  |  |  |  |
| average | 425.00 | 376.67 | 244.67 | 501.50 | 501.50 |
| Line + Gaba. | 491 | 367 | 160 | 220 | 306 |
| Line + Gaba. | 421 | 360 | 264 | 286 | 315 |
| Line + Gaba. | 350 | 312 | 165 | 272 | 244 |
| Line + Gaba. | 499 | 378 | 287 | 225 |  |
| average | 440.25 | 354.25 | 219 | 250.75 | 288.33333 |
| tTEST | 0.3740275 | 0.316937 | 0.278281 | 0.028344 | 0.0340366 |

|  | FLC4 | HepG2 | LS-180 | H3B | 2215 |
| --- | --- | --- | --- | --- | --- |
| Line | 47 | 470 | 297 | 437 | 413 |
| Line | 48 | 456 | 599 | 521 | 555 |
| Line | 136 | 475 | 305 | 543 |  |
| Line | 264 |  | 537 | 439 |  |
| average | 123.75 | 467.00 | 434.50 | 485.00 | 484 |
| Line + Gaba. | 104 | 526 | 498 | 230 | 361 |
| Line + Gaba. | 277 | 512 | 555 | 194 | 466 |
| Line + Gaba. | 201 | 515 | 528 | 402 | 529 |
| Line + Gaba. |  |  | 450 |  |  |

TABLE 1-continued

Gabaculine decreases HCC cell proliferation
HCC Lines Proliferation CPM-B with Gabaculine (20000 umol/L)

|  | | | | | |
|---|---|---|---|---|---|
| average | 194 | 517.6667 | 507.75 | 275.3333 | 452 |
| tTEST | 0.1865 | 0.001358 | 0.212675 | 0.032269 | 0.373485 |

TABLE 2

Gabaculine significantly decreased AFP secretion in HCC cells

|  | ct-26 | PLC | FLC-4 | HEPG2 | LS180 | HEP3B | 2215.00 | SKHEP1 | HEPAI6 | HUH7 |
|---|---|---|---|---|---|---|---|---|---|---|
| line | 0.00 | 6.03 | 0.38 | 5.70 | 0.00 | 12.02 | 1569.40 | 0.00 | 0.00 | 318.46 |
| line | 0.03 | 6.27 | 0.43 | 5.76 | 0.04 | 12.06 | 1486.20 | 0.00 | 0.00 | 243.00 |
| line |  | 5.84 | 0.36 | 5.81 | 0.00 |  | 1520.90 | 0.00 | 0.00 | 291.21 |
| average | 0.02 | 6.05 | 0.39 | 5.76 | 0.01 | 12.04 | 1525.50 | 0.00 | 0.00 | 284.22 |
| line + ga. | 0.00 | 5.99 | 0.41 | 5.80 | 0.00 | 10.42 | 1601.20 | 0.00 | 0.02 | 282.71 |
| line + ga. | 0.03 | 5.85 | 0.38 | 5.79 | 0.00 | 10.42 | 1522.00 | 0.00 | 0.00 | 234.53 |
| line + ga. | 0.00 | 5.40 | 0.42 | 5.29 |  | 10.27 | 1554.80 | 0.00 | 0.00 | 281.06 |
| average | 0.01 | 5.75 | 0.40 | 5.63 | 0.00 | 10.37 | 1559.33 | 0.00 | 0.01 | 266.10 |
| tTEST | 0.4044 | 0.1236 | 0.3078 | 0.2613 | 0.2113 | 0.0001 | 0.1837 | #DIV/0! | 0.2113 | 0.2721 |

Therefore, in vitro, Gabaculine (20000 umole/litter) treatment, significantly suppressed HCC cell line growth.

Example 3

In Vivo Administration of Gabaculine Significantly Suppressed Tumor Growth

The surprising decrease in proliferation of different HCC cell lines, as a result of treatment with OAT inhibitor, encouraged the present inventors to further explore the possible effect of such inhibition on tumor growth. Therefore, the in vivo effect of OAT inhibition on tumor growth was examined using Hep3B HCC-transplanted athymic Balb/c mice. Mice (n=8/group) were injected once with 500 µg/kg of Gabaculine followed 48 hrs later by AFP serum levels measurement. PBS was injected to a matched control group.

As shown by Table 3, in vivo administration of Gabaculine significantly suppressed tumor growth. Within seven days of treatment, AFP serum levels decreased by 92% (207,888 to 22,172 pg/ml), in comparison with 9.7 fold increase (278,220 to 2,146,927 pg/ml) in treated vs. controls, respectively ($p<0.05$).

TABLE 3 in-vivo treatment with Gabaculine

Group (A) = PBS

|  | Day 0 AFP(1) | Day 2 (48 hr. after treatment AFP(2) | Day 7 AFP(3) AFTER TREATMENT | AFP(3)/ AFP(2) |
|---|---|---|---|---|
| A-1 | 2992 | 347180 | 9039000 | 26.03549 |
| A-2 | 5874 | 737100 | 6768000 | 9.181929 |
| A-4 | 523 | 45110 | 58210 | 1.290401 |
| A-5 | 1138 | 721300 | 53610 | 0.074324 |
| A-6 | 2199 | 198500 | 98100 | 0.494207 |
| A-7 | 435 | 105150 | 263400 | 2.504993 |
| A-9 | 13 | 22390 | 818600 | 36.56096 |
| A-10 | 129 | 49030 | 76500 | 1.560269 |
| Average | 1662.875 | 278220 | 2146927.5 | 9.712822 |

TABLE 3-continued in-vivo treatment with Gabaculine

Group (B + C) = GABACULINE

|  | Day 0 AFP(1) | Day 2 AFP(2) | Day 7 AFP(3) AFTER TREATMENT |  |
|---|---|---|---|---|
| B-1 | 19920 | 1004600 | 12210 | 0.012154 |
| B-2 | 1331 | 86260 | 325980 |  |
| B-5 | 301 | 64500 | 4350 | 0.067442 |
| B-6 | 1900 | 158130 | 96600 | 0.61089 |
| B-7 | 3430 | 667600 | 32710 | 0.048996 |
| B-9 | 833 | 59920 | 1500 | 0.025033 |
| B-10 | 989 | 181110 | 10950 | 0.06046 |
| C-2 | 486 | 28710 | 90 | 0.003135 |
| C-3 | 3032 | 248780 | 58420 | 0.234826 |
| C-5 | 7014 | 434600 | 17260 | 0.039715 |
| C-9 | 399 | 43820 | 30 | 0.000685 |
| C-10 | 2994 | 283530 | 35060 | 0.123655 |
| Average | 2785 | 207888 | 22172 | 0.080403 |

In vivo administration of one dose of Gabaculine resulted in suppression of HCC growth. These results suggest that OAT plays an important role in HCC growth and may serve as a potential therapeutic target.

Example 4

Inhibition of OAT Using Different Concentrations of Gabaculine Analogue 8 (LHJ-II-79), Leads to Inhibition of AFP Secretion from HCC Cell Lines Encouraged by the in vitro and in vivo results of inhibiting OAT using Gabaculine, the inventors next examined the in vitro effect of a further OAT inhibitor, Gabaculine analogue 8 (LHJ-II-79), on AFP secretion from two different HCC cell lines. Therefore, Hep3b and HepG2 hepatocellular carcinoma cell lines were detached from culture dishes using trypsin-EDTA, re-plated in triplicates in 12 well culture dishes ($1\times10^5$ cells/well) and incubated at 37° C. Gabaculine analogue 8 was added to wells at varying concentrations (0.1 µg/ml, 1 µg/ml, 10 µg/ml and 50 µg/ml). After 48 hours, cell supernatant was analyzed for AFP concentration.

As clearly shown by Table 4, treatment of both CCC cell lines resulted in significant reduction of AFP secretion by the cells. This effect was concentration dependent. These results clearly demonstrate the feasibility of using the Gabaculine analogue 8 (LHJ-II-79), for treating hepatocellular carcinoma.

TABLE 4

Gabaculine analogue 8 (LHJ-II-79) decreases αFP secretion by HCC cell lines

EXP. I

| analogue no. | conc. of analogue | HCC cell line | AVG results AF ng/ml H3B 1:5 dil, HG2 1:100 dil |
|---|---|---|---|
| CONTROL | — | Hep3b | 42.52 |
| 8 | 10 ug/ml | Hep3b | 37.96 |
| 8 | 50 ug/ml | Hep3b | 18.52 |
| CONTROL | — | HepG2 | 34.19 |
| 8 | 10 ug/ml | HepG2 | 37.98 |
| 8 | 50 ug/ml | HepG2 | 23.54 |

Exp. II

| analogue no. | conc. of analogue | HCC cell line | AVG results AF ng/ml H3B 1:5 dil, HG2 1:100 dil |
|---|---|---|---|
| CONTROL | — | Hep3b | 13.42 |
| 8 | 0.1 ug/ml | Hep3b | 12.66 |
| 8 | 1 ug/ml | Hep3b | 11.92 |
| 8 | 10 ug/ml | Hep3b | 9.63 |
| 8 | 50 ug/ml | Hep3b | 9.37 |
| CONTROL | — | HepG2 | 11.93 |
| 8 | 0.1 ug/ml | HepG2 | 11.92 |
| 8 | 1 ug/ml | HepG2 | 12.85 |
| 8 | 10 ug/ml | HepG2 | 11.38 |
| 8 | 50 ug/ml | HepG2 | 8.54 |

EXP. III

| analogue no. | conc. of analogue | HCC cell line | AVG results AF ng/ml H3B 1:5 dil, HG2 1:100 dil |
|---|---|---|---|
| CONTROL | — | Hep3b | 11.39 |
| 8 | 10 ug/ml | Hep3b | 10.97 |
| 8 | 50 ug/ml | Hep3b | 6.98 |
| CONTROL | — | HepG2 | 12.07 |
| 8 | 10 ug/ml | HepG2 | 10.67 |
| 8 | 50 ug/ml | HepG2 | 7.57 |

EXP. IV

| analogue no. | conc. of analogue | HCC cell line | AVG results AF ng/ml H3B 1:2 dil, HG2 1:50 dil |
|---|---|---|---|
| CONTROL | — | Hep3b | 18.45 |
| 8 | 10 ug/ml | Hep3b | 13.73 |

TABLE 4-continued

Gabaculine analogue 8 (LHJ-II-79) decreases αFP secretion by HCC cell lines

| 8 | 50 ug/ml | Hep3b | 11.30 |
|---|---|---|---|
| CONTROL | — | HepG2 | 13.32 |
| 8 | 10 ug/ml | HepG2 | 12.74 |
| 8 | 50 ug/ml | HepG2 | 8.94 |

Example 5

In Vivo Administration of Gabaculine Analogue 8 (LHJ-II-79) for Suppression of Tumor Growth The inventors further explore the possible effect of Gabaculine analogue 8 (LHJ-II-79) on tumor growth. Therefore, the in vivo effect of this inhibitor is examined using Hep3B HCC-transplanted athymic Balb/c mice. Mice (n=8/group) are injected once with 0.1 to 100 μg/kg of Gabaculine analogue 8 (LHJ-II-79) followed 48 hrs later by AFP serum levels and tumor development (tumor size) measurements. PBS is injected to a matched control group.

The invention claimed is:

1. A method for the treatment of a malignant pathologic proliferative disorder in a subject in need thereof, comprising the step of selectively inhibiting the enzymatic activity of ornithine aminotransferase (OAT) by administering to said subject an inhibitory effective amount of OAT inhibitor, wherein said inhibitor is any one of Gabaculine analogue 8 (LHJ-II-79) and 5-amino-1,3-hexadienyl-carboxylic acid (Gabaculine) and wherein said malignant pathologic proliferative disorder is hepatocellular carcinoma (HCC).

2. The method according to claim 1, wherein said inhibitor is 5-amino-1,3-hexadienyl-carboxylic acid (Gabaculine).

3. The method according to claim 1, wherein said inhibitor is Gabaculine analogue 8 (LHJ-II-79).

4. The method according to claim 1, wherein inhibiting the expression of ornithine aminotransferase (OAT) is performed by administering to said subject an inhibitory effective amount of a nucleic acid molecule comprising at least one target specific sequence, which sequence is complementary to a target ribonucleotide sequence comprised within OAT mRNA and wherein said nucleic acid molecule is selected from the group consisting of an antisense DNA or RNA molecule, a ribonucleic acid molecule having endonuclease activity (ribozyme) and a small interfering RNA (siRNA) specific for said OAT.

5. A method for the treatment of hepatocellular carcinoma (HCC) in a subject in need thereof, comprising the step of administering to said subject a therapeutically effective amount of Gabaculine analogue 8 (LHJ-II-79).

6. A method for the treatment of hepatocellular carcinoma (HCC) in a subject in need thereof, comprising the step of administering to said subject a therapeutically effective amount of 5-amino-1,3-hexadienyl-carboxylic acid (Gabaculine).

* * * * *

UNITED STATES PATENT AND TRADEMARK OFFICE
CERTIFICATE OF CORRECTION

| | | |
|---|---|---|
| PATENT NO. | : 8,211,865 B2 | Page 1 of 1 |
| APPLICATION NO. | : 12/377889 | |
| DATED | : July 3, 2012 | |
| INVENTOR(S) | : Ilan et al. | |

It is certified that error appears in the above-identified patent and that said Letters Patent is hereby corrected as shown below:

In the Specification

Column 1, line 15, should read:
-- This invention was made with government support under grant number GM066132 awarded by the National Institutes of Health. The government has certain rights in the invention. --

Signed and Sealed this
Twenty-fifth Day of February, 2014

Michelle K. Lee
*Deputy Director of the United States Patent and Trademark Office*